US010390528B2

United States Patent
Richardson

(10) Patent No.: US 10,390,528 B2
(45) Date of Patent: *Aug. 27, 2019

(54) SOLID AGROFORMULATIONS FOR PREPARING NEAR MICRO-EMULSION AQUEOUS PESTICIDES

(71) Applicant: BASF Corporation, Florham Park, NJ (US)

(72) Inventor: Ronald O. Richardson, St. Louis, MO (US)

(73) Assignee: BASF Corporation, Florham Park, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/426,669

(22) Filed: Feb. 7, 2017

(65) Prior Publication Data

US 2017/0142961 A1 May 25, 2017

Related U.S. Application Data

(63) Continuation of application No. 14/651,472, filed as application No. PCT/US2013/074453 on Dec. 11, 2013, now Pat. No. 9,686,980.

(60) Provisional application No. 61/897,018, filed on Oct. 29, 2013, provisional application No. 61/736,151, filed on Dec. 12, 2012.

(30) Foreign Application Priority Data

Dec. 18, 2012 (EP) .................................. 12197917

(51) Int. Cl.
| A01N 25/14 | (2006.01) |
| A01N 25/30 | (2006.01) |
| A01N 51/00 | (2006.01) |
| A01N 25/04 | (2006.01) |
| A01N 25/12 | (2006.01) |
| A01N 53/00 | (2006.01) |
| A01N 43/36 | (2006.01) |
| A01N 43/56 | (2006.01) |
| A01N 47/44 | (2006.01) |

(52) U.S. Cl.
CPC ............ *A01N 25/14* (2013.01); *A01N 25/04* (2013.01); *A01N 25/12* (2013.01); *A01N 25/30* (2013.01); *A01N 43/36* (2013.01); *A01N 43/56* (2013.01); *A01N 47/44* (2013.01); *A01N 51/00* (2013.01); *A01N 53/00* (2013.01)

(58) Field of Classification Search
CPC ....................................................... A01N 25/14
USPC ......................................................... 514/471
See application file for complete search history.

(56) References Cited

U.S. PATENT DOCUMENTS

| 4,289,525 A | 9/1981 | Pasarela et al. |
| 4,776,881 A | 10/1988 | Mostafa |
| 4,779,881 A | 10/1988 | Baker |
| 5,709,871 A * | 1/1998 | Hill .................. A01N 25/14 424/409 |
| 6,872,689 B1 * | 3/2005 | Misselbrook .......... A01N 47/36 504/128 |
| 6,893,589 B1 * | 5/2005 | Misselbrook .......... A01N 25/14 264/115 |
| 9,686,980 B2 * | 6/2017 | Richardson ............ A01N 51/00 |
| 2004/0011262 A1 | 1/2004 | Fujita et al. |
| 2010/0317525 A1 * | 12/2010 | Hidalgo ................. A01N 41/10 504/231 |
| 2011/0053776 A1 * | 3/2011 | Bahr ...................... A01N 25/00 504/271 |
| 2011/0067612 A1 | 3/2011 | Ito et al. |

FOREIGN PATENT DOCUMENTS

| CA | 1209363 A | 8/1986 | |
| CN | 1065181 A | 10/1992 | |
| CN | 1131899 A | 9/1996 | |
| CN | 1408222 A | 4/2003 | |
| CN | 1988799 A | 6/2007 | |
| CN | 102805080 A | 12/2012 | |
| EP | 0501798 B | 8/1977 | |
| EP | 0120427 B1 | 12/1988 | |
| EP | 0 501 798 A1 * | 2/1992 | ............. A01N 25/14 |
| EP | 0638235 A1 | 2/1995 | |
| EP | 720427 B1 | 6/1998 | |
| JP | 52-030577 B | 8/1977 | |
| JP | H10109905 A | 4/1998 | |
| JP | 2001114603 A | 4/2001 | |
| JP | 2001206802 A | 7/2001 | |
| JP | 2003040702 A | 2/2003 | |
| JP | 2003252702 A | 9/2003 | |
| JP | 2005008619 A | 1/2005 | |
| JP | 2009073820 A | 4/2009 | |
| JP | 2009523131 A | 6/2009 | |
| JP | 2010018603 A | 1/2010 | |
| WO | 9215197 A1 | 9/1992 | |
| WO | 9508265 A1 | 3/1995 | |
| WO | 9834482 A1 | 8/1998 | |
| WO | 2006038631 A1 | 4/2006 | |
| WO | 2007133522 A2 | 11/2007 | |
| WO | 2008008180 A2 | 1/2008 | |
| WO | 2009064702 A2 | 5/2009 | |

OTHER PUBLICATIONS

EPA Pesticide Fact Sheet (2004).*
Dietmar Kores: "Principal ®—Blendtechnologie von Rimsulfuron und Nicosulfuron für überlegene Gräserwirkung in Mais." Österreichische PS-Tagung 2010, Dec. 2, 2010, pp. 1-22.
International Search Report for PCT/US2013/074453, dated Feb. 18, 2014, 5 pages.

(Continued)

*Primary Examiner* — Nizal S Chandrakumar
(74) *Attorney, Agent, or Firm* — Armstrong Teasdale LLP

(57) ABSTRACT

Disclosed are extruded pesticide granules that when mixed with water form a near micro-emulsion that is highly stable. The extruded pesticide granules include at least one pesticide active ingredient, a non-ionic surfactant, and a carrier, which is desirably urea powder or urea pearl. Processes for making the extruded pesticide granules are also disclosed.

12 Claims, No Drawings

(56) References Cited

OTHER PUBLICATIONS

International Search Report and Written Opinion for PCT/US2013/074447, dated Feb. 24, 2014, 13 pages.
International Preliminary Report on Patentability for PCT/US2013/074453, dated Feb. 11, 2015, 18 pages.
Database WPI Week 200171, Thomson Scientific, London, GB, XP002720417, AN 2001-613621, 4 pages.
European Search Report for EP Patent Application No. 18203661.6, dated Jan. 25, 2019, 5 pages.
World Health Organization (available online at www.who.int; accessed Jan. 19, 2017).
Komaki Tomoo et al, Urea fertilizer containing agrochemicals, Chemical Abstracts Service, 1978, Columbus, OH, US.

* cited by examiner

SOLID AGROFORMULATIONS FOR PREPARING NEAR MICRO-EMULSION AQUEOUS PESTICIDES

CROSS-REFERENCE TO RELATED APPLICATIONS

This application claims priority to International Application Number PCT/US2013/074453 filed Dec. 11, 2013, and claims priority to U.S. patent application Ser. No. 14/651,472 filed Jun. 11, 2015, U.S. Patent Application No. 61/736,151 filed Dec. 12, 2012, EP Patent Application 12197917.3 filed Dec. 18, 2012, and U.S. Patent Application 61/897,018 filed Oct. 29, 2013, the disclosures of which are hereby expressly incorporated by reference in their entireties.

FIELD OF THE DISCLOSURE

The present disclosure relates to solid agroformulations and methods of preparing the same. More particularly, the present disclosure relates to extruded pesticide granules including a urea carrier and at least one pesticide active agent that when mixed with water form long term stable near micro-emulsions suitable for pesticide application. The present disclosure also relates to methods of preparing and using the solid agroformulations.

BACKGROUND OF THE DISCLOSURE

Crop and pest protection agents have conventionally been formulated in solid or liquid compositions, usually in the form of a concentrate for ease of handling and transportation. The concentrate is generally diluted with water by the user before application. Many liquid formulations in the form of emulsifiable or near-emulsifiable concentrates may contain a very high proportion of organic solvents (often up to 80 percent), which are increasingly coming under scrutiny for their potential negative effect on the environment.

Water-based suspension concentrates, which are another conventionally available form, are often viscous giving rise to handling problems and loss of active ingredient through retention in the packaging. Solid formulations, which may also be commercially available, can also have disadvantages; the more common granules and powders in particular can be difficult to measure but more importantly can be dusty and pose inhalation hazards for the formulator and the user. Tablets have not been used extensively because they are often slow to dissolve. In addition, solid formulations have been found generally to possess a lower biological activity than liquid formulations. Also, with unsophisticated mixing techniques at the site of use, the tendency of solid forms not to disperse immediately can cause not only clogging of spray equipment with undispersed formulation, but also an inadequate application of active ingredient to the crop or area to be treated.

Based on the foregoing, there is a need for fast-dispersing, solid pesticide formulations which have improved handling characteristics and enhanced biological activity over conventional forms, to satisfy both environmental concerns and provide an effective pesticidal product with commercially acceptable levels of stability for long term use.

SUMMARY OF THE DISCLOSURE

The present disclosure is directed to solid agroformulations, and in particular extruded pesticide granules, and liquid aqueous pesticide formulations including these granules. The extruded pesticide granules include a urea carrier in combination with a non-ionic surfactant, at least one pesticide active ingredient, and a small amount of residual water. This novel combination of components, when extruded as described herein, rapidly dissolves in room temperature water with gentle agitation to form a near micro-emulsion that has only a very slight haze that is substantially resistant to settling out of materials. In many embodiments, the extruded pesticide granules as described herein will dissolve in two minutes or less in room temperature water with gentle agitation. Because of these significant dissolution properties and the formation of a near micro-emulsion and retardation of settling for many days, the extruded pesticide granules described herein may be easily mixed and used "on site" thus improving the usefulness of the agroformulation. Additionally, various extruded pesticide granules including different pesticide active agents may easily be used in combination to form "on site" or other customized blends of two or more pesticide active agents to address various problems with a single aqueous formulation.

The present disclosure is further directed to an extruded pesticide granular composition comprising urea, a non-ionic surfactant, a pesticide active ingredient, and water.

The present disclosure is further directed to an extruded pesticide granule comprising from about 70 wt. % to about 80 wt. % urea pearls, from about 5 wt. % to about 10 wt. % of a non-ionic surfactant having a molecular weight of from about 14,000 to about 15,000 Daltons, from about 5 wt. % to about 10 wt. % pesticide active ingredient, and less than 3% water.

The present disclosure is further directed to a process for preparing an extruded pesticide granule. The process comprises melting a non-ionic surfactant, dissolving a pesticide active into the molten non-ionic surfactant, introducing urea, adding water, and mixing to form a mixture, extruding the mixture to form an extrudate, and drying the extrudate to form the extruded pesticide granule.

The present disclosure is further directed to a process for preparing an extruded pesticide granule. The process comprises introducing urea into water to substantially wet the urea, introducing a substantially water soluble pesticide active agent into the wetted urea, adding a nonionic surfactant to produce a mixture, extruding the mixture to form an extrudate, and drying the extrudate to form the extruded pesticide granule.

The present disclosure is further directed to an aqueous pesticide composition comprising at least one substantially water soluble pesticide active agent, wherein the aqueous pesticide composition is a near micro-emulsion.

The present disclosure is further directed to an extruded pesticide granular composition. The composition comprises first extruded pesticide granules and second extruded pesticide granules, wherein the first extruded pesticide granules include a pesticide different from a pesticide in the second extruded pesticide granules.

The present disclosure is further directed to a method for controlling phytopathogenic fungi and/or undesired vegetation and/or undesired attack by insects or mites and/or for regulating the growth of plants, where an extruded pesticide granular composition of the present disclosure is allowed to act on the respective pests, their environment or on the crop plants to be protected from the respective pests, on the soil and/or on undesired plants and/or on the crop plants and/or their environment.

It has been unexpectedly found that extruded pesticide granules that form highly desirable and stable near micro-emulsions in water can be suitably produced with one or more substantially soluble or substantially insoluble pesticide active agents in combination with a urea-based carrier material and a non-ionic surfactant. Surprisingly, by incorporating urea as the carrier material, the extruded pesticide granule has excellent dissolution/dispersion characteristics in water and forms a near micro-emulsion with only a very slight haze that is stable for many days upon mixing. Additionally, a suitable amount of the extruded pesticide granule can be incorporated into water in two minutes or less with only gentle agitation. Importantly, either water-soluble or water-insoluble, or a combination of both, pesticide active ingredients can be used in the disclosed extruded pesticide granules.

Additionally, the extruded pesticide granules and methods of the present disclosure provide numerous other advantages, including improved biological efficacy and lower dose rates for controlling pests; ability to be easily prepared to be organic compound-free; and ability to be easily transported to a work site and mixed with water onsite for easy and convenient application. Also, through the use of the specific components described herein for preparing the extruded pesticide granules, an approximate 66% reduction in the amount of water used during extrusion can be obtained without any negative impact on the resulting product. This has a positive environmental impact.

Furthermore, it has been unexpectedly found that in many embodiments the energy from the extrusion process used to form the extruded pesticide granules results in the dissolution of additional urea within the formulation, which moderates the temperature by slightly cooling the mixture. After the extrusion is complete, the slight excess urea in the solution begins to re-crystallize, thus releasing heat. This heat release gradually warms the extruded granules to actually assist in the drying process of the extruded granules. Such warming has been unexpectedly found to dry the granules to a water lever of about 3% to about 4% (by weight). This self-drying reduces the amount of overall drying required to produce the final extruded pesticide granule.

DETAILED DESCRIPTION OF THE DISCLOSURE

The extruded pesticide granules of the present disclosure provide for an easily mixable pesticide granule that dissolves/suspends in water at suitable pesticide concentrations to form a near micro-emulsion that this stable for many days or even a week. The extruded pesticide granules include one or more pesticide active ingredients in combination with a non-ionic surfactant and urea, optionally in the form or urea pearls. This unique combination of components is easily extruded to form the extruded pesticide granules that have numerous desirable characteristics and uses. In many embodiments of the present disclosure, the extruded pesticide granules are organic solvent-free extruded pesticide granules.

The extruded granules as described herein may include a substantially water soluble pesticide active agent, a substantially water insoluble pesticide active agent, or a combination of a substantially water soluble pesticide active agent and a substantially water insoluble pesticide active agent. Because the extruded granules can be formulated to include a single pesticide active agent, or various combinations of two or more pesticide active agents, the present disclosure provides a cost effective and simple means for providing customized blends of extruded pesticide granules including two or more pesticide active agents that, when combined with water, form a near micro-emulsion that is stable for application and includes a desired customized blend of pesticide active agents. The extruded pesticide granules also allow for easy transport as they are granular solids that do not need to be transported in water, thus reducing the weight of the product for transport and allowing multiple different types of granules (i.e., granules with different pesticide active agents) to be easily transported, mixed together, introduced into water, and utilized. In some embodiments, a near micro-emulsion aqueous pesticide combination may be formulated by including two or more different extruded granules that include different pesticide active agents.

These and other optional elements or limitations of the extruded pesticide granules and methods of the present disclosure are described in detail hereinafter.

The term "near micro-emulsion" as used herein refers to an aqueous pesticide active agent-containing solution that, upon preparation and for a period of at least 24 hours, forms a slightly hazy, substantially sediment-free solution that light can pass through, but through which objects cannot be made out. When compared to a micro-emulsion, which includes solutions that are clear and through which objects can easily be made out, and an emulsion, which is milky and through which light does not pass through and objects cannot be made out, a "near micro-emulsion" falls in between these two and is in its own class of emulsions.

The term "pesticide" as used herein refers to at least one active substance selected from the group of the fungicides, insecticides, nematicides, herbicides, safeners, growth regulators and combinations thereof. Preferred pesticides for use within the scope of the present disclosure include fungicides, insecticides, and herbicides.

Numerical ranges as used herein are intended to include every number and subset of numbers within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All combinations of method or process steps as used herein can be performed in any order, unless otherwise specified or clearly implied to the contrary by the context in which the referenced combination is made.

The extruded pesticide granules and corresponding manufacturing methods and uses of the present disclosure can comprise, consist of, or consist essentially of the essential elements and limitations of the disclosure as described herein, as well as any additional or optional ingredients, components, or limitations described herein or otherwise useful in pesticide applications.

Pesticide Active Ingredient

The extruded pesticide granules described herein include at least one pesticide active ingredient. In some embodiments, the extruded pesticide granules will include two, three or more pesticide active ingredients. Suitable pesticide active ingredients include both substantially water-soluble (pesticide has a solubility in water of at least 10 g/L, preferably at least 25 g/L, and in particular at least 35 g/L) and substantially water-insoluble (pesticide has a solubility in water of up to 10 g/L, including up to 2 g/L, and in particular up to 0.5 g/L at 20 C) pesticide active ingredients, although the pesticide active ingredient should be substantially or completely soluble in the non-ionic surfactant described herein such that there is no milling required of the pesticide active ingredient. Insecticide active ingredients are particularly preferred within the scope of the present disclosure.

Suitable pesticide active ingredients can be found, for example, in the Pesticide Manual, 15th Ed. (2009), The British Crop Protection Council, London. Examples of pesticides may be selected from the following list (A to L are fungicides):

A) Respiration Inhibitors

Inhibitors of complex III at Qo site (e.g. strobilurins): azoxystrobin, coumethoxystrobin, cou moxystrobin, dimoxystrobin, enestroburin, fenaminstrobin, fenoxystrobin/flufenoxystrobin, fluoxastrobin, kresoxim-methyl, metominostrobin, orysastrobin, picoxystrobin, pyraclostrobin, pyrametostrobin, pyraoxystrobin, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)-phenyl)-2-methoxyimino-N-methyl-acetamide, pyribencarb, triclopyri carb/chlorodincarb, famoxadone, fenamidone;

Inhibitors of complex III at Qi site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl] 2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate;

Inhibitors of complex II (e. g. carboxamides): benodanil, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, N-[9-(dichloromethylene)-1,2,3,4-tetrahydro-1,4-methanonaphthalen-5-yl]-3-(difluoromethyl)-1-methyl-1H-pyrazole-4-carboxamide;

Other respiration inhibitors (e.g. complex I, uncouplers): diflumetorim, (5,8-difluoroquinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentinsalts, such as fentin-acetate, fentin chloride or fentin hydroxide; ametoctradin; and silthiofam;

B) Sterol Biosynthesis Inhibitors (SBI Fungicides)

C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole; imidazoles: imazalil, pefurazoate, prochloraz, triflumizol; pyrimidines, pyridines and piperazines: fenarimol, nuarimol, pyrifenox, triforine;

Delta14-reductase inhibitors: aldimorph, dodemorph, dodemorph-acetate, fenpropimorph, tridemorph, fenpropidin, piperalin, spiroxamine;

Inhibitors of 3-keto reductase: fenhexamid;

C) Nucleic Acid Synthesis Inhibitors

Phenylamides or acyl amino acid fungicides: benalaxyl, benalaxyl-M, kiralaxyl, metalaxyl, metalaxyl-M (mefenoxam), ofurace, oxadixyl;

Others: hymexazole, octhilinone, oxolinic acid, bupirimate, 5-fluorocytosine, 5-fluoro-2-(ptolylmethoxy) pyrimidin-4-amine, 5-fluoro-2-(4-fluorophenylmethoxy)pyrimidin-4-amine;

D) Inhibitors of Cell Division and Cytoskeleton

Tubulin inhibitors, such as benzimidazoles, thiophanates: benomyl, carbendazim, fuberidazole, thiabendazole, thiophanate-methyl; triazolopyrimidines: 5-chloro-7-(4-methyl-piperidin-1-yl)-6-(2,4,6-trifluorophenyl)-[1,2,4]triazolo[1,5-a]pyrimidine Other cell division inhibitors: diethofencarb, ethaboxam, pencycuron, fluopicolide, zoxamide, metrafenone, pyriofenone;

E) Inhibitors of Amino Acid and Protein Synthesis

Methionine synthesis inhibitors (anilino-pyrimidines): cyprodinil, mepanipyrim, pyrimethanil;

Protein synthesis inhibitors: blasticidin-S, kasugamycin, kasugamycin hydrochloride-hydrate, mildiomycin, streptomycin, oxytetracyclin, polyoxine, validamycin A;

F) Signal Transduction Inhibitors

MAP/histidine kinase inhibitors: fluoroimid, iprodione, procymidone, vinclozolin, fenpiclonil, fludioxonil;

G protein inhibitors: quinoxyfen;

G) Lipid and Membrane Synthesis Inhibitors

Phospholipid biosynthesis inhibitors: edifenphos, iprobenfos, pyrazophos, isoprothiolane; Lipid peroxidation: dicloran, quintozene, tecnazene, tolclofos-methyl, biphenyl, chloroneb, etridiazole;

Phospholipid biosynthesis and cell wall deposition: dimethomorph, flumorph, mandipropamid, pyrimorph, benthiavalicarb, iprovalicarb, valifenalate and N-(1-(1-(4-cyanophenyl)-ethanesulfonyl)-but-2-yl) carbamic acid-(4-fluorophenyl) ester;

Compounds affecting cell membrane permeability and fatty acids: propamocarb, propamocarb-hydrochlorid H) Inhibitors with Multi Site Action Inorganic active substances: Bordeaux mixture, copper acetate, copper hydroxide, copperoxychloride, basic copper sulfate, sulfur;

Thio- and dithiocarbamates: ferbam, mancozeb, maneb, metam, metiram, propineb, thiram, zineb, ziram;

Organochlorine compounds (e.g. phthalimides, sulfamides, chloronitriles): anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-Nethyl-4-methyl-benzenesulfonamide;

Guanidines and others: guanidine, dodine, dodine free base, guazatine, guazatine-acetate, iminoctadine, iminoctadine-triacetate, iminoctadine-tris(albesilate), dithianon;

I) Cell Wall Synthesis Inhibitors inhibitors of glucan synthesis: validamycin, polyoxin B; melanin synthesis inhibitors: pyroquilon, tricyclazole, carpropamid, dicyclomet, fenoxanil;

J) Plant Defense Inducers

Acibenzolar-S-methyl, probenazole, isotianil, tiadinil, prohexadione-calcium; phosphonates: fosetyl, fosetyl-aluminum, phosphorous acid and its salts;

K) Unknown Mode of Action

Bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxin-copper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluoro-phenyl)-methyl)-2-phenyl acetamide, N'-(4-(4-chloro- 3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-Nethyl-N-methyl formamidine, 2-{1-[2-(5-methyl-3-trifluoromethyl-pyrazole-1-yl)-acetyl]-piperidin-4-yl}-thiazole-4-carboxylic acid methyl-(1,2,3,4-tetrahydro-naphthalen-1-yl)-amide, 2-{1-[2-(5-methyl-3-trifluoromethyl-pyrazole-1-yl)-acetyl]-piperidin-4-yl}-thiazole-4-carboxylic acid methyl-(R)-1,2,3,4-tetrahydro-naphthalen-1-yl-amide, 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, methoxy-acetic acid 6-tert-butyl-8-fluoro-2,3-dimethyl-quinolin-4-yl ester, N-Methyl-2-{1-[(5-methyl-3-trifluoromethyl-1H-pyrazol-1-yl)-acetyl]-piperidin-4-yl}-N-[(1R)-1,2,3,4-tetrahydronaphthalen-1-yl]-4-thiazolecarboxamide, 3-[5-(4-methylphenyl)-2,3-dimethyl-isoxazolidin-3-yl]-pyridine, 3-[5-(4-chloro-phenyl)-2,3-dimethyl-isoxazolidin-3-yl]-pyridine (pyrisoxazole), N-(6-methoxy-pyridin-3-yl) cyclopropanecarboxylic acid amide, 5-chloro-1-(4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide;

L) Antifungal Biocontrol Agents, Plant Bioactivators: *Ampelomyces quisqualis* (e.g. AQ 10® from Intrachem Bio GmbH & Co. KG, Germany), *Aspergillus flavus* (e.g. AFLAGUARD® from Syngenta, CH), *Aureobasidium pullulans* (e.g. BOTECTOR® from bio-ferm GmbH, Germany), *Bacillus pumilus* (e.g. NRRL Accession No. B-30087 in SONATA® and BALLAD®
Plus from AgraQuest Inc., USA), *Bacillus subtilis* (e.g. isolate NRRL-Nr. B-21661 in RHAPSODY®, SERENADE® MAX and SERENADE® ASO from AgraQuest Inc., USA), *Bacillus subtilis* var. *amyloliquefaciens* FZB24 (e.g. TAEGRO® from Novozyme Biologicals, Inc., USA), *Candida oleophila* I-82 (e.g. ASPIRE® from Ecogen Inc., USA), *Candida saitoana* (e.g. BIOCURE® (in mixture with lysozyme) and BIOCOAT® from Micro Flo Company, USA (BASF SE) and Arysta), Chitosan (e.g. ARMOUR-ZEN from BotriZen Ltd., NZ), *Clonostachys rosea* f. *catenulata*, also named *Gliocladium catenulatum* (e.g. isolate J1446: PRESTOP® from Verdera, Finland), *Coniothyrium minitans* (e.g. CONTANS® from Prophyta, Germany), *Cryphonectria parasitica* (e.g. *Endothia parasitica* from CNICM, France), Cryptococcusalbidus (e.g. YIELD PLUS® from Anchor Bio-Technologies, South Africa), Fusariumoxysporum (e.g. BIOFOX® from S.I.A.P.A., Italy, FUSACLEAN® from Natural Plant Protection, France), *Metschnikowia fructicola* (e.g. SHEMER® from Agrogreen, Israel), *Microdochium dimerum* (e.g. ANTIBOT® from Agrauxine, France), *Phlebiopsis gigantea* (e.g. ROTSOP® from Verdera, Finland), *Pseudozyma flocculosa* (e.g. SPORODEX® from Plant Products Co. Ltd., Canada), *Pythium oligandrum* DV74 (e.g. POLYVERSUM® from Remeslo SSRO, Biopreparaty, Czech Rep.), *Reynoutria sachlinensis* (e.g. REGALIA® from Marrone BioInnovations, USA), *Talaromyces flavus* V117b (e.g. PROTUS® from Prophyta, Germany), *Trichoderma asperellum* SKT-1 (e.g. ECO-HOPE® from Kumiai Chemical Industry Co., Ltd., Japan), *T. atroviride* LC52 (e.g. SENTINEL® from Agrimm Technologies Ltd, NZ), *T. harzianum* T-22 (e.g. PLANTSHIELD® der Firma BioWorks Inc., USA), *T. harzianum* TH 35 (e.g. ROOT PRO® from Mycontrol Ltd., Israel), *T. harzianum* T-39 (e.g. TRICHODEX® and *TRICHODERMA* 2000® from Mycontrol Ltd., Israel and Makhteshim Ltd., Israel), *T. harzianum* and *T. viride* (e.g. TRICHOPEL from Agrimm Technologies Ltd, NZ), *T. harzianum* ICC012 and *T. viride* ICC080 (e.g. REMEDIER® WP from Isagro Ricerca, Italy), *T. polysporum* and *T. harzianum* (e.g. BINAB® from BINAB Bio-Innovation AB, Sweden), *T. stromaticum* (e.g. TRICOVAB® from C.E.P.L.A.C., Brazil), *T. virens* GL-21 (e.g. SOILGARD® from Certis LLC, USA), *T. viride* (e.g. TRIECO® from Ecosense Labs. (India) Pvt. Ltd., In dien, BIO-CURE® F from T. Stanes & Co. Ltd., Indien), *T. viride* TV1 (e.g. *T. viride* TV1 from Agribiotec srl, Italy), *Ulocladium oudemansii* HRU3 (e.g. BOTRY-ZEN® from Botry-Zen Ltd, NZ);

M) Growth Regulators

Abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadionecalcium), prohydrojasmon, thidiazuron, triapenthenol, tributyl phosphorotrithioate, 2,3,5-tri-iodobenzoic acid, trinexapac-ethyl and uniconazole;

N) Herbicides

Acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;

Amino acid derivatives: bilanafos, glyphosate, glufosinate, sulfosate;

Aryloxyphenoxypropionates: clodinafop, cyhalofop-butyl, fenoxaprop, fluazifop, haloxyfop, metamifop, propaquizafop, quizalofop, quizalofop-P-tefuryl;

Bipyridyls: diquat, paraquat;

(thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;

Cyclohexanediones: butroxydim, clethodim, cycloxydim, profoxydim, sethoxydim, tepraloxydim, tralkoxydim;

Dinitroanilines: benfluralin, ethalfluralin, oryzalin, pendimethalin, prodiamine, trifluralin;

Diphenyl ethers: acifluorfen, aclonifen, bifenox, diclofop, ethoxyfen, fomesafen, lactofen, oxyfluorfen;

Hydroxybenzonitriles: bomoxynil, dichlobenil, ioxynil;

Imidazolinones: imazamethabenz, imazamox, imazapic, imazapyr, imazaquin, imazethapyr;

Phenoxy acetic acids: clomeprop, 2,4-dichlorophenoxyacetic acid (2,4-D), 2,4-DB, dichlorprop, MCPA, MCPA-thioethyl, MCPB, Mecoprop;

Pyrazines: chloridazon, flufenpyr-ethyl, fluthiacet, norflurazon, pyridate;

Pyridines: aminopyralid, clopyralid, diflufenican, dithiopyr, fluridone, fluroxypyr, picloram, picolinafen, thiazopyr;

Sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxy-pyrimidin-2-yl)urea;

Triazines: ametryn, atrazine, cyanazine, dimethametryn, ethiozin, hexazinone, metamitron, metribuzin, prometryn, simazine, terbuthylazine, terbutryn, triaziflam;
Ureas: chlorotoluron, daimuron, diuron, fluometuron, isoproturon, linuron, methabenzthiazuron, tebuthiuron;
Other acetolactate synthase inhibitors: bispyribac-sodium, cloransulam-methyl, diclosulam, florasulam, flucarbazone, flumetsulam, metosulam, ortho-sulfamuron, penoxsulam, propoxy carbazone, pyribambenz-propyl, pyribenzoxim, pyriftalid, pyriminobac-methyl, pyrimisulfan, pyrithiobac, pyroxasulfone, pyroxsulam;
Others: amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, *Drechslera monoceras*, endothal, ethofumesate, etobenzanid, fenoxasulfone, fentrazamide, flumiclorac-pentyl, flumioxazin, flupoxam, flurochloridone, flurtamone, indanofan, isoxaben, isoxaflutole, lenacil, propanil, propyzamide, quinclorac, quinmerac, mesotrione, methyl arsenic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-5 3,6-dihydro-2Hpyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methylphenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester.

O) Insecticides
Organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methylparathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;
Carbamates: alanycarb, aldicarb, bendiocarb, benfuracarb, carbaryl, carbofuran, carbosul fan, fenoxycarb, furathiocarb, methiocarb, methomyl, oxamyl, pirimicarb, propoxur, thiodicarb, triazamate;
Pyrethroids: allethrin, bifenthrin, cyfluthrin, cyhalothrin, cyphenothrin, cypermethrin, alphacypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, py rethrin I and II, resmethrin, silafluofen, tau-fluvalinate, tefluthrin, tetramethrin, tralomethrin, transfluthrin, profluthrin, dimefluthrin;
Insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

Nicotinic receptor agonists/antagonists compounds: clothianidin, dinotefuran, flupyradifurone, imidacloprid, thiamethoxam, nitenpyram, acetamiprid, thiacloprid, 1-(2-chloro-thiazol-5-ylmethyl)-2-nitrimino-3,5-dimethyl-[1,3,5] triazinane; GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioicacid amide;
Macrocyclic lactone insecticides: abamectin, emamectin, milbemectin, lepimectin, spinosad, spinetoram;
Mitochondrial electron transport inhibitor (METI) I acaricides: fenazaquin, pyridaben, tebufenpyrad, tolfenpyrad, flufenerim;
METI II and III compounds: acequinocyl, fluacyprim, hydramethylnon; Uncouplers: chlorfenapyr;
Oxidative phosphorylation inhibitors: cyhexatin, diafenthiuron, fenbutatin oxide, propargite;
Moulting disruptor compounds: cryomazine;
Mixed function oxidase inhibitors: piperonyl butoxide;
Sodium channel blockers: indoxacarb, metaflumizone;
Others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluron, dinotefuran, and pyrifluquinazon.

Preferred pesticide active ingredients are pyraclostrobin, metconazole, alpha-cypermethrin, boscalid, dinotefuran, Chlorfenapyr, epoxiconazole and combinations thereof. In some embodiments, a preferred pesticide active ingredient will be a pesticide active ingredient that is substantially, or wholly, soluble in the molten non-ionic surfactant described below.

The pesticide active ingredient may be present in the extruded pesticide granules in an amount of from about 1 wt. % to about 25 wt. %, including from about 5 wt. % to about 25 wt. %, including from about 10 wt. % to about 25 wt. %, including from about 10 wt. % to about 20 wt. %, including from about 15 wt. % to about 20 wt. %. In one specific embodiment, the pesticide active ingredient may be present in the extruded pesticide granules in an amount of about 20 wt. %. In other specific embodiments, the pesticide active ingredient may be present in an amount of from about 1 wt. % to about 50 wt. %, including from about 10 wt. % to about 50 wt. %.

Non-Ionic Surfactant

The extruded pesticide granules of the present disclose additionally include at least one non-ionic surfactant, which acts as a lubricant during the extrusion process described herein and swells when it becomes wet. The non-ionic surfactant is desirably a non-ionic amphiphilic polyalkoxylate surfactant free of ionic groups that has a melting point of 55° C. or more. The polyalkoxylate is amphiphilic, which usually means that is has surfactant properties and lowers the surface tension of water. Usually, the polyalkoxylate is obtainable by alkoxylation using alkyleneoxides, such as C2-C6-alkylene oxide, preferably ethylene oxide, propylene oxide, or butylene oxide. Examples of suitable polyalkoxylates are block polymers or compounds such as alcohols, alkylphenols, amines, amides, arylphenols, fatty acids or fatty acid esters which have been alkoxylated with 1 to 50 equivalents.

The non-ionic surfactant may have a melting point of at least 35° C., preferably at least 43° C., more preferably at least 48° C. and in particular at least 50° C. and in particular at least 55° C.

The non-ionic surfactant is usually substantially soluble in water at 20° C. Desirably, the solubility in water of the non-ionic surfactant is at least 3 wt %, more preferably at least 7 wt %, and in particular at least 10 wt %.

The molecular weight of the non-ionic surfactant is typically in the range of from about 5,000 to about 50,000 Daltons, desirably from about 2,000 to about 35,000 Daltons, and desirably from about 5,000 to about 20,000 Daltons In one particular embodiment, the molecular weight of the non-ionic surfactant is from about 14,000 Daltons to about 15,000 Daltons.

The non-ionic surfactant is desirably a block polymer, which may contain a hydrophilic block and a hydrophobic block. Suitable block polymers are block polymers of the A-B or A-B-A type comprising blocks of polyethylene oxide and polypropylene oxide, or of the A-B-C type comprising alkanol, polyethylene oxide and polypropylene oxide. Desirably, the non-ionic surfactant is a block polymer comprising at least one polyethoxylate block and at least one poly-C3-C5-alkoxylate block (e.g. polypropoxylate or polybutoxylate). In particular, the non-ionic surfactant may be a triblock polymer of A-B-A type comprising a polyethoxylate type A block and a poly-C3-C5-alkoxylate block (preferably polypropoxylate) type B block.

One particularly preferred non-ionic surfactant for use in the extruded pesticide granules of the present disclosure is Pluronic F127 (BASF Germany).

The non-ionic surfactant may be present in the extruded pesticide granules in an amount of from about 5 wt. % to about 20 wt. %, including from about 5 wt. % to about 10 wt. %, including from about 7 wt. % to about 10 wt. %.

In some desirable embodiments, the weight ratio of non-ionic surfactant to pesticide active ingredient is about 1:1.

Solid Carrier

The extruded pesticide granules of the present disclosure include one or more solid carriers. Some suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, methylcellulose, starch; fertilizers, e.g. ammonium sulfate, ammonium phosphate, ammonium nitrate; products of vegetable origin, e.g. cereal meal, tree bark meal, wood meal, nutshell meal; sugars, e.g. mono- or di saccharides, and mixtures thereof. Some useful solid carriers are mono- or di-saccharides, polysaccharides, and mixtures thereof.

A particularly suitable and desirable solid carrier is urea, which may optionally be in the form of urea powder or urea pearls (commercially available from Cole-Parmer or Acros Organics). Urea is highly soluble in water, and cools down upon dissolution in water to improve the overall solubility of components through its interaction with the non-ionic surfactant described above. In many embodiments, the urea will have a particle size of less than or equal to 60 mesh or even 50 mesh, or even 40 mesh, or even 30 mesh.

The carrier material, and in many desirable embodiments the urea carrier material, is generally present in the extruded pesticide granules in an amount of at least 50 wt. %, including at least 60 wt. %, including at least 70 wt. %, including at least 80 wt. %. In some embodiments, the urea carrier material may be present in the extruded pesticide granules in an amount of from about 50 wt. % to about 95 wt. %, including from about 70 wt. % to about 90 wt. %, including from about 70 wt. % to about 80 wt. %, and including about 80 wt. %. In some other embodiments, the urea carrier material may be present in the extruded pesticide granules in an amount of from about 40 wt. % to about 80 wt. %.

Solvent

The extruded pesticide granules of the present disclosure generally include a small amount solvent that is utilized during the extrusion process. Generally, the vast majority of the solvent utilized in the extrusion process is removed in the drying of the granules step; however, it is generally not possible or always desirable to completely remove all of the solvent and, as such, the dried granules will contain a small trace of solvent in many embodiments.

Suitable solvents and liquid carriers for use in the extrusion processes described herein are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, 15 gamma-butyrolactone; fatty acids; phosphonates; amines; amides, e.g. N-methylpyrrolidone, fatty acid dimethylamides; and mixtures thereof. A particularly suitable and desirable solvent is water. When water is used as the solvent, the resulting extruded pesticide granule is substantially or completely organic compound-free.

Typically, the dried extruded pesticide granules will include up to 5 wt % solvents and liquid carriers (e.g. water), desirably up to 3 wt %, and in particular up to 1 wt %. In some embodiments, the extruded pesticide granules will include less than 0.8 wt. %, including less than 0.5 wt. %, including less than 0.2 wt. % solvent (water).

Optional Components/Auxiliaries

The extruded pesticide granules may optionally comprise other components or auxiliaries to facilitate the manufacturing or processing characteristics of the granules, or otherwise improve one or more properties thereof. Some suitable auxiliaries are additional surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers, effervescents, and binders.

Suitable effervescent is a combination of a hydrogen carbonate and an organic acid, such as a combination of citric acid and potassium hydrogencarbonate. Examples of the hydrogen carbonate include sodium hydrogen carbonate, potassium hydrogen carbonate and ammonium hydrogen carbonate. Examples of the organic acid include citric acid, succinic acid, malic acid, lactic acid, tartaric acid, fumaric acid and maleic acid. The organic acid is preferably used in an amount of 0.5 percent by weight to 20 percent by weight and, particularly, 1 percent by weight to 10 percent by weight based on the whole weight. The organic acid may be used alone or as a mixture of two or more of them. The hydrogencarbonate can be preferably used in an amount of 0.25 times to 2 times by molar ratio of the amount of the organic acid.

Suitable surfactants are surface-active compounds, such as anionic, cationic, nonionic and amphoteric surfactants, polyelectrolytes, and mixtures thereof. Preferred surfactants are anionic surfactants. Such surfactants can be used as emulsifier, dispersant, solubilizer, wetter, penetration enhancer, protective colloid, or adjuvant. Examples of surfactants are listed in McCutcheon's, Vol. 1: Emulsifiers &

Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a negligible or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Preferred adjuvants are non-ionic surfactants selected from alkoxylates. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. More preferred adjuvants are linear or branched, aliphatic C6-C20-alkanols, which have been alkoxylated with ethylene oxide and optionally with propylene oxide.

Suitable thickeners are polysaccharides (e.g. xanthan gum, carboxymethylcellulose), anorganic clays (organically modified or unmodified), polycarboxylate thickeners, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Manufacture of Extruded Pesticide Granules

The extruded pesticide granules described herein and capable forming a near micro-emulsion upon introduction into water and gentle agitation, can be manufactured using a conventional low pressure extrusion apparatus, including a low pressure dome extruder. In some embodiments, high pressure extruders may also be utilized within the scope of the present disclosure to produce suitable extruded pesticide granules.

In embodiments of the present disclosure where at least one substantially water-insoluble pesticide active agent is utilized (or a combination of at least one substantially water-insoluble pesticide active agent and a substantially water-soluble pesticide active agent), to prepare an extrudable mix for extrusion and subsequent drying, the surfactant or surfactants may be first melted at elevated temperature to provide a molten surfactant composition. A suitable temperature may be, for example, about 90 C. Into the molten surfactant is added the pesticide active ingredient, or pesticide active ingredient. The pesticide active ingredient (or active ingredients, if there is more than one) is mixed into the molten surfactant until the pesticide active ingredient is dissolved into the surfactant and a substantially homogeneous mixture is obtained.

Once a substantially homogeneous mixture of the molten surfactant and pesticide active ingredient is obtained, the carrier material (desirably urea in the form of powdered urea or urea pearls in many embodiments) is mixed in to prepare a substantially homogeneous mixture. Once this is completed, the desired amount of water is added and the resulting mixture thoroughly mixed and kneaded. Generally, from about 4 grams to about 10 grams, including from about 4 grams to about 8 grams, and desirably about 6 grams of water is added for each 100 grams of non-ionic surfactant, pesticide active ingredient, and carrier material (urea), to achieve the desired moisture content for extrusion of the mixture. This amount of water produces a damp powder that can then be suitably extruded through a low pressure dome extruder using, for example, a dome screen size of from about 0.5 mm to about 1.5 mm, including about 1.0 mm, depending upon the desired granule size. The temperature of the extruder may be, for example, from about 60° F. to about 100° F., including about 80° F. The resulting granules may then be dried using conventional means to produce the extruded pesticide granules that have a high solubility in water due to the formation of a near micro-emulsion.

In other embodiments where a substantially water soluble pesticide active agent is utilized, to prepare an extrudable mix for extrusion and subsequent drying, the carrier material (desirably urea in the form of powdered urea or urea pearls in many embodiments) is first mixed with a solvent, such as water, and the solvent is allowed to wet and partially dissolve the carrier material. It is desirable that the solvent completely wet out the carrier material for efficient granule formation. The carrier material (typically urea) is completely wetted in the formulation when the temperature quits dropping and begins to warm up. Thorough mixing is desirable. In many embodiments, the amount of solvent (typically water) will be between about 3% and about 5% of the total weight of all of the components utilized to formulate the extruded granules, as urea dissolves up to about 150% (by weight) in water.

Once the carrier material has been completely wetted with the solvent, the substantially water soluble pesticide active agent is mixed in to prepare a substantially homogeneous mixture. The substantially water soluble pesticide active agent will de-lump and disperse into the carrier material/solvent mixture as it slightly dissolves. After thorough mixing, a surfactant or surfactants is added to gel the slight excess solvent and prevent a "stiff dough" formation to desirably prepare a damp powder or wet cake that easily flows. The surfactant or surfactants also act as a lubricant for extrusion.

This damp powder or flowable wet cake can then be suitably extruded through a low pressure dome extruder as described above. The extrusion energy applied to the damp powder results in slightly more urea dissolving, which moderates the temperature by slightly cooling, which assists in keeping the temperature steady. After extrusion, the slight excess urea in the solution begins to recrystallize thereby releasing heat. The extruded granules then actually warm up and can dry themselves to the 3% (by weight) to 4% (by weight) range. The resulting granules may then be further dried using conventional means to produce the extruded pesticide granules that have a high solubility in water due to the formation of a near micro-emulsion.

These dried extruded pesticide granules can be used to prepare an aqueous tank mix, in which a pesticide in near micro-emulsion form wherein the particle size is generally below 1.0 micrometer, by introducing the extruded granules into water and applying gentle agitation. In many embodiments, the particle size will be less than 0.8 micrometers, or even less than 0.7 micrometers, or even less than 0.5 micrometers.

The dried extruded pesticide granules can be introduced into water to prepare the aqueous tank mix such that the resulting near micro-emulsion tank mix has a total pesticide active agent concentration level of from about 0.1% (by weight) to about 1% (by weight), including about 0.5% (by weight). In other embodiments, the near micro-emulsion tank mix may have a total pesticide active agent concentration of at least 0.05% (by weight), including at least 0.06% (by weight), including at least 0.07% (by weight), including at least 0.08% (by weight). The exact concentration of total pesticide active agent, as well as the number of different pesticide active agents present (from extruded granules including different pesticide active agents), may differ based on the desired use of the aqueous formation.

The mixing of the extruded pesticide granules and water may be done directly in a spraying apparatus containing a tank, or multiple tanks. The mixing may be done at a temperature of from about 5 C to about 50 C, desirably from about 10 C to about 30 C. The mixing may be done by adding the solid composition to the water already present in a tank and agitating.

The methods of the present disclosure further include methods of controlling phytopathogenic fungi and/or undesired plant growth and/or undesired attack by insects or mites and/or for regulating the growth of plants, where the extruded pesticide granules obtained by the methods as described herein are allowed to act upon the particular pests, their habitat or the plants to be protected from the particular pest, the soil and/or on undesired plants and/or the useful plants and/or their habitat.

A user may apply the extruded pesticide granules after preparing an aqueous tank mix usually from a pre-dosage device, a knapsack sprayer, a spray tank, a spray plane, or an irrigation system. In some embodiments, the agrochemical composition is made up with water, buffer, and/or further auxiliaries to the desired application concentration and the ready-to-use spray composition is obtained.

The disclosure furthermore relates to a method for controlling phytopathogenic fungi and/or undesired vegetation and/or undesired attack by insects or mites and/or for regulating the growth of plants, where the concentrate according to the invention or the emulsion according to the invention is allowed to act on the respective pests, their environment or on the crop plants to be protected from the respective pests, on the soil and/or on undesired plants and/or on the crop plants and/or their environment. In general, the therapeutic treatment of humans and animals is excluded from the method for controlling phytopathogenic fungi and/or undesired vegetation and/or undesired attack by insects or mites and/or for regulating the growth of plants.

When employed in crop protection, the application rates of the pesticides amount is from 0.001 to 2 kg per ha, preferably from 0.005 to 2 kg per ha, especially preferably from 0.05 to 0.9 kg per ha and in particular from 0.1 to 0.75 kg per ha, depending on the nature of the desired effect. In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kg of plant propagation material (preferably seed) are generally required. When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, welters, adjuvants, fertilizers or micronutrients and further pesticides (for example herbicides, insecticides, fungicides, growth regulators, safeners) may be added to the emulsion in the form of a premix or optionally only shortly before use (tank mix). These agents can be admixed to the compositions according to the disclosure at a weight ratio of from 1:100 to 100:1, preferably from 1:10 to 10:1.

The user applies the composition according to the disclosure usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the disclosure is thus obtained. Usually, 20 to 2000 liters, preferably 50 to 400 liters, of the ready-to-use spray liquor are applied per hectare of agricultural useful area.

The present embodiments are to be considered in all respects as illustrative and not restrictive and that all changes and equivalents also come within the description of the present disclosure. The following non-limiting examples will further illustrate the extruded pesticide compositions and methods of the present disclosure.

EXAMPLES

The following examples illustrate specific embodiments and/or features of the extruded pesticide granules of the present disclosure. The examples are given solely for the purpose of illustration and are not to be construed as limitations of the present disclosure, as many variations thereof are possible without departing from the spirit and scope of the disclosure. In addition to the specific components set forth in the Examples, each dried extruded pesticide granule described included a small amount of residual water, typically less than 2 wt. %, and more typically less than 1 wt. %.

Example 1

In this Example, extruded pesticide granules including one pesticide active agent suitable for preparing a near micro-emulsion in water were prepared.

20.00 grams of Pluronic F-127 non-ionic surfactant was melted at 90° C. to prepare a molten surfactant. To this molten surfactant was added 20.06 grams of alpha-cypermethrin and the resulting mixture stirred to provide a substantially homogeneous mixture of pesticide active and surfactant. To this substantially homogenous mixture was added 159.94 grams of urea (98% pearls) and the resulting blend kneaded well to produce a substantially homogenous mixture of pesticide active, surfactant, and urea. To this homogeneous mixture was added 12.0 grams of water and the resulting blend was mixed well. This produced a damp powder extrudable composition.

The damp powder was then extruded using a low pressure dome extruder having a 1 mm dome screen at a temperature of about 81° F. The resulting granules were dried at room temperature on a glass plate. The resulting dried granules had a specific gravity of about 0.5, and a cylindrical shape (about 1.2 mm×about 3 mm). The granules were about 10.03 wt. % pesticide active, about 10.0 wt. % non-ionic surfactant, and about 79.97 wt. % urea. The extruded granules can be added directly to water with gentle agitation to form a near micro-emulsion.

Example 2

In this Example, extruded pesticide granules including two pesticide active agents suitable for preparing a near micro-emulsion in water were prepared.

20.00 grams of Pluronic F-127 non-ionic surfactant was melted at 80° C. to prepare a molten surfactant. To this molten surfactant was added 20.24 grams of alpha-cypermethrin and the resulting mixture stirred to provide a substantially homogeneous mixture of pesticide active and surfactant. To this substantially homogenous mixture was added 119.31 grams of urea (98% pearls) and the resulting blend kneaded well until cool to produce a substantially homogenous mixture of pesticide active, surfactant, and urea. To this homogeneous mixture was uniformly blended in 40.44 grams of dinotefuran. To this uniformly blended mixture was added 6.0 grams of water and the resulting blend was mixed well. This produced a damp powder extrudable composition.

The damp powder was then extruded using a low pressure dome extruder having a 0.8 mm dome screen at a temperature of about 81° F. The resulting granules were dried at room temperature on a glass plate. The resulting dried granules had a specific gravity of about 0.5, and a cylindrical shape (about 1.2 mm×about 3 mm). The granules were about 10.12 wt. % alpha cypermethrin, about 10.0 wt. % non-ionic surfactant, about 20.22 wt. % dinotefuran, and about 59.65 wt. % urea. The extruded granules can be added directly to water with gentle agitation to form a near micro-emulsion.

Example 3

In this Example, extruded pesticide granules including one pesticide active agent suitable for preparing a near micro-emulsion in water were prepared.

20.00 grams of Pluronic F-127 non-ionic surfactant was melted at 80° C. to prepare a molten surfactant. To this molten surfactant was added 20.53 grams of chlorfenapyr and the resulting mixture stirred to provide a substantially homogeneous mixture of pesticide active and surfactant. To this substantially homogenous mixture was added 159.47 grams of urea (98% pearls) and the resulting blend kneaded well to produce a substantially homogenous mixture of pesticide active, surfactant, and urea. To this homogeneous mixture was added 6.0 grams of water and the resulting blend was mixed well. This produced a damp powder extrudable composition.

The damp powder was then extruded using a low pressure dome extruder having a 0.8 mm dome screen at a temperature of about 81° F. The resulting granules were dried at room temperature on a glass plate. The resulting dried granules had a specific gravity of about 0.5, and a cylindrical shape (about 1.2 mm×about 3 mm). The granules were about 10.27 wt. % pesticide active, about 10.0 wt. % non-ionic surfactant, and about 79.73 wt. % urea. The extruded granules can be added directly to water with gentle agitation to form a near micro-emulsion.

Example 4

In this Example, extruded pesticide granules including one pesticide active agent suitable for preparing a near micro-emulsion in water were prepared.

40.00 grams of Pluronic F-127 non-ionic surfactant was melted at 80° C. to prepare a molten surfactant. To this molten surfactant was added 41.67 grams of permethrin and the resulting mixture stirred to provide a substantially homogeneous mixture of pesticide active and surfactant. To this substantially homogenous mixture was added 118.33 grams of urea (98% pearls) and the resulting blend kneaded well to produce a substantially homogenous mixture of pesticide active, surfactant, and urea. To this homogeneous mixture was added 12.0 grams of water and the resulting blend was mixed well. This produced a damp powder extrudable composition.

The damp powder was then extruded using a low pressure dome extruder having a 1 mm dome screen at a temperature of about 81° F. The resulting granules were dried at room temperature on a glass plate. The resulting dried granules had a specific gravity of about 0.5, and a cylindrical shape (about 1.2 mm×about 3 mm). The granules were about 20.83 wt. % pesticide active, about 20.0 wt. % non-ionic surfactant, and about 59.17 wt. % urea. The extruded granules can be added directly to water with gentle agitation to form a near micro-emulsion.

Example 5

In this Example, extruded pesticide granules including one pesticide active agent suitable for preparing a near micro-emulsion in water were prepared.

20.00 grams of Pluronic F-127 non-ionic surfactant was melted at 80° C. to prepare a molten surfactant. To this molten surfactant was added 22.54 grams of fipronil and the resulting mixture stirred to provide a substantially homogeneous mixture of pesticide active and surfactant. To this substantially homogenous mixture was added 157.46 grams of urea (98% pearls) and the resulting blend kneaded well to produce a substantially homogenous mixture of pesticide active, surfactant, and urea. To this homogeneous mixture was added 12.0 grams of water and the resulting blend was mixed well. This produced a damp powder extrudable composition.

The damp powder was then extruded using a low pressure dome extruder having a 0.8 mm dome screen at a temperature of about 81° F. The resulting granules were dried at room temperature on a glass plate. The resulting dried granules had a specific gravity of about 0.5, and a cylindrical shape (about 1.2 mm×about 3 mm). The granules were about 11.27 wt. % pesticide active, about 10.0 wt. % non-ionic surfactant, and about 78.73 wt. % urea. The extruded granules can be added directly to water with gentle agitation to form a near micro-emulsion.

Example 6

In this Example, extruded pesticide granules including one pesticide active agent suitable for preparing a near micro-emulsion in water were prepared.

10.00 grams of Pluronic F-127 non-ionic surfactant was melted at 65° C. to prepare a molten surfactant. To this molten surfactant was added 10.53 grams of lambda cyhalothrin and the resulting mixture stirred to provide a substantially homogeneous mixture of pesticide active and surfactant. To this substantially homogenous mixture was added 74.47 grams of urea (98% pearls) and the resulting blend kneaded well to produce a substantially homogenous mixture of pesticide active, surfactant, and urea. To this homogeneous mixture was added 12.0 grams of water and the resulting blend was mixed well. This produced a damp powder extrudable composition.

The damp powder was then extruded using a low pressure dome extruder having a 1.2 mm dome screen at a temperature of about 81° F. The resulting granules were dried at room temperature on a glass plate. The resulting dried granules had a specific gravity of about 0.5, and a cylindrical shape (about 1.2 mm×about 3 mm). The granules were about 10.56 wt. % pesticide active, about 10.0 wt. % non-ionic surfactant, and about 79.47 wt. % urea. The extruded granules can be added directly to water with gentle agitation to form a near micro-emulsion.

Example 7

In this Example, the biological residual efficacy of extruded pesticide granules of the present disclosure was tested and compared to the efficacy of Phantom Termiticide-Insecticide and a control. Specifically, extruded pesticide granules as prepared in Example 3 and including about 10 wt. % chlorfenapyr and extruded pesticide granules as prepared in Example 3 and including about 20 wt. % chlorfenapyr we evaluated and compared to the Phantom and control (control was no chemical treatment).

The pesticides were tested against German cockroaches (*Blattella germanica*), bed bugs (*Cimex lectularius*), confused flour beetles (*Tribolium castaneum*), and house crickets (*Acheta domesticus*). This testing was a residual test on unpainted plywood and painted plywood (Behr white semi-gloss exterior paint). The insects were confined on the treated surfaces with various cups depending on the insect. Four replications were used with ten insects for each replication. The knockdown and mortality were recorded over time, as shown in the following Tables 1-4. Each test formulation was diluted with water to a 0.5 wt. % active level and applied with a DeVibiss atomizer set at 10 psi from 12 inches at the rate of 1 gallon of product per 1000 square feet. Both the extruded pesticide granules of the present disclosure tested form a near micro-emulsion in water. The tests were discontinued when the control mortality was above 20%.

TABLE 1

Percent Mortality of German Cockroaches at Time in Days

| | | Aged Day 1 | | | | Aged Days 28 | | | |
|---|---|---|---|---|---|---|---|---|---|
| Product | Surface | 1 | 2 | 3 | 5 | 1 | 2 | 3 | 5 |
| Phantom SC | Unpainted | 3.3 | 76.7 | 100.0 | — | 66.7 | 100.0 | — | — |
| Chlorfenapyr 10% WMG | | 16.7 | 96.7 | 100.0 | — | 50.0 | 96.7 | 100.0 | — |
| Chlorfenapyr 20% WMG | | 50.0 | 100.0 | 100.0 | — | 83.3 | 100.0 | — | — |
| Control | | 3.3 | 6.7 | 10.0 | — | 0.0 | 0.0 | 3.3 | — |
| Phantom SC | Painted | 3.3 | 66.7 | 100.0 | 100.0 | 6.7 | 63.3 | 93.3 | — |
| Chlorfenapyr 10% WMG | | 8.3 | 50.0 | 90.0 | 100.0 | 3.3 | 50.0 | 93.3 | |
| Chlorfenapyr 20% WMG | | 6.7 | 63.3 | 96.7 | 100.0 | 6.7 | 53.3 | 93.3 | — |
| Control | | 0.0 | 3.3 | 3.3 | 10.0 | 0.0 | 6.7 | 10.0 | 66.7 |

TABLE 2

Percent Mortality of Bed Bugs at Time in Days

| | | Aged Day 1 | | | | | Aged Days 28 | | | |
|---|---|---|---|---|---|---|---|---|---|---|
| Product | Surface | 1 | 2 | 3 | 5 | 7 | 1 | 2 | 3 | 5 |
| Phantom SC | Unpainted | 0.0 | 10.0 | 10.0 | 30.7 | 41.1 | 3.3 | 10.0 | 26.7 | — |
| Chlorfenapyr 10% WMG | | 16.1 | 55.2 | 64.5 | 71.5 | 87.3 | 23.3 | 33.3 | 43.3 | — |
| Chlorfenapyr 20% WMG | | 3.3 | 33.3 | 43.3 | 76.7 | 83.3 | 16.7 | 36.7 | 50.0 | — |
| Control | | 0.0 | 0.0 | 3.3 | 3.3 | 6.7 | 0.0 | 3.3 | 16.7 | 33.3 |
| Phantom SC | Painted | 0.0 | 6.7 | 20.0 | 40.0 | 53.3 | 12.9 | — | — | — |
| Chlorfenapyr 10% WMG | | 30.0 | 46.7 | 50.0 | 83.3 | 96.7 | 42.2 | — | — | — |
| Chlorfenapyr 20% WMG | | 0.0 | 23.3 | 33.3 | 86.7 | 93.3 | 24.6 | — | — | — |
| Control | | 0.0 | 0.0 | 3.3 | 6.7 | 16.7 | 23.3 | 26.7 | — | — |

TABLE 3

Percent Mortality of Confused Flour Beetles at Time in Days

| | | Aged Day 1 | | | | Aged Days 28 | | | |
|---|---|---|---|---|---|---|---|---|---|
| Product | Surface | 1 | 2 | 3 | 5 | 1 | 2 | 3 | 5 |
| Phantom SC | Unpainted | 33.3 | 90.0 | — | — | 83.3 | 100.0 | — | — |
| Chlorfenapyr 10% WMG | | 58.7 | 95.8 | — | — | 96.7 | 100.0 | — | — |
| Chlorfenapyr 20% WMG | | 83.6 | 100.0 | — | — | 93.3 | 100.0 | — | — |
| Control | | 0.0 | 0.0 | — | — | 0.0 | 0.0 | 0.0 | — |
| Phantom SC | Painted | 26.7 | 90.0 | — | — | 20.0 | 93.3 | 93.3 | 100.0 |
| Chlorfenapyr 10% WMG | | 12.4 | 70.9 | — | — | 50.0 | 86.7 | 90.0 | 100.0 |
| Chlorfenapyr 20% WMG | | 37.0 | 96.7 | — | — | 46.7 | 96.7 | 96.7 | 100.0 |
| Control | | 0.0 | 0.0 | — | — | 0.0 | 0.0 | 6.7 | 13.3 |

TABLE 4

Percent Mortality of House Crickets at Time in Days

| | | Aged Day 1 | | | | Aged Days 28 | | | |
|---|---|---|---|---|---|---|---|---|---|
| Product | Surface | 1 | 2 | 3 | 5 | 1 | 2 | 3 | 5 |
| Phantom SC | Unpainted | 70.0 | 90.0 | — | — | 70.8 | 95.0 | — | — |
| Chlorfenapyr 10% WMG | | 90.0 | 100.0 | — | — | 51.7 | 90.0 | — | — |
| Chlorfenapyr 20% WMG | | 100.0 | 100.0 | — | — | 95.0 | 100.0 | — | — |
| Control | | 5.0 | 20.0 | — | — | 0.0 | 10.0 | 20.0 | — |
| Phantom SC | Painted | 90.0 | 100.0 | — | — | 20.0 | 85.0 | 85.0 | — |
| Chlorfenapyr 10% WMG | | 91.7 | 100.0 | — | — | 90.8 | 100.0 | — | — |
| Chlorfenapyr 20% WMG | | 90.0 | 100.0 | — | — | 39.2 | 100.0 | — | — |
| Control | | 0.0 | 0.0 | — | — | 9.2 | 14.2 | 14.2 | 19.2 |

As shown in the Tables 1-4 above, for cockroaches all of the treatments were effective (>90%) of both surfaces at 1 and 28 days after treatment. For bed bugs, the bed bugs were not controlled (not >90%) by Phantom SC. Both of the extruded pesticide granule formulation of the present disclosure performed well at 1 day after treatment. For the confused flour beetles, all of the treatments worked on both surfaces at day 1, with the exception of the 10% extruded pesticide granule on painted wood; however at 28 days after treatment, all of the products worked well on both surfaces. For the house crickets, all of the treatments worked on both surfaces at day 1. At day 30, the extruded pesticide granule formulations worked well on both surfaces while the Phantom SC worked well on the unpainted wood and did not work well on the painted wood.

Example 8

In this Example, a contact test for biological efficacy of extruded pesticide granules of the present disclosure was tested and compared to the efficacy of Phantom Termiticide-Insecticide and a control. Specifically, extruded pesticide granules as prepared in Example 3 and including about 10 wt. % chlorfenapyr and extruded pesticide granules as prepared in Example 3 and including about 20 wt. % chlorfenapyr we evaluated and compared to the Phantom and control (control was no chemical treatment).

The pesticides were tested against German cockroaches (*Blattella germanica*) and bed bugs (*Cimex lectularius*). This testing was a contact test. The insects were confined in cups, treated and moved to clean cups. Four replications were used with ten insects for each replication. The knock-down and mortality were recorded over time as shown in Tables 1-2. Each test formulation was diluted with water to a 0.25% or a 0.5 wt. % active level and applied with a DeVibiss atomizer set at 10 psi from 12 inches at the rate of 1 gallon of product per 1000 square feet. Both the extruded pesticide granules of the present disclosure tested form a near micro-emulsion in water.

TABLE 1

Percent Mortality of German Cockroaches at Time

| | | Hours | |
|---|---|---|---|
| Product | Rate | 4 | 24 |
| Phantom SC | 0.25% | 2.5 | 100.0 |
| Chlorfenapyr 10% WMG | 0.25% | 0.0 | 100.0 |
| Chlorfenapyr 20% WMG | 0.25% | 0.0 | 100.0 |
| Phantom SC | 0.5% | 7.5 | 97.5 |
| Chlorfenapyr 10% WMG | 0.5% | 22.5 | 100.0 |
| Chlorfenapyr 20% WMG | 0.5% | 12.5 | 100.0 |
| Control | — | 0.0 | 0.0 |

TABLE 2

Percent Mortality of Bed Bugs at Time

| | | | Hours | | Days | | |
|---|---|---|---|---|---|---|---|
| Product | Rate | Reps | 4 | 24 | 2 | 3 | 5 |
| Phantom SC | 0.25% | 3 | 7.2 | 17.4 | 26.8 | 44.3 | 68.1 |
| Chlorfenapyr 10% WMG | 0.25% | 4 | 0.0 | 14.1 | 33.2 | 54.8 | 76.4 |
| Chlorfenapyr 20% WMG | 0.25% | 4 | 0.0 | 15.0 | 27.5 | 45.0 | 50.0 |
| Control | — | 1 | 0.0 | 0.0 | 0.0 | 0.0 | 0.0 |

As shown in Tables 1-2, for cockroaches all three of the product were effective (>90%) at both dilution rates at 24 hours after treatment. For bed bugs, the bed bugs were not controlled (not >90%) by the Phantom or the extruded pesticide granules. At 5 days after treatment the Phantom and the 10% extruded pesticide granule had the best control.

Example 9

In this Example, extruded pesticide granules including one substantially water soluble pesticide active agent suitable for preparing a pesticide active agent-containing near micro-emulsion in water were prepared.

159.94 grams of urea (98% pearls) was introduced into 10 grams of water and then thoroughly mixed to allow the water to completely wet out the urea. Once the wetting of the urea was complete, 20.06 grams of dinotefuran was blended into the water/urea wetted mixture and mixed thoroughly. After mixing, 20 grams of Pluronic F-127 non-ionic surfactant was introduced and thoroughly mixed to produce a flowable wet cake that was suitable for extrusion.

The flowable wet cake was then extruded using a low pressure dome extruder having a 1 mm dome screen at a temperature of about 81° F. The resulting granules were dried at room temperature on a glass plate. The resulting dried granules had a specific gravity of about 0.5, and a cylindrical shape (about 1.2 mm×about 3 mm). The granules were about 10.03 wt. % pesticide active, about 10.0 wt. % non-ionic surfactant, and about 79.97 wt. % urea. The extruded granules can be added directly to water with gentle agitation to form a near micro-emulsion pesticide solution.

What is claimed is:

1. A process for preparing an extruded pesticide granule comprising introducing urea into water to wet the urea, introducing a substantially water soluble pesticide active agent into the wetted urea, adding a nonionic surfactant to produce a damp mixture, extruding the damp mixture to form an extrudate, and drying the extrudate to form the extruded pesticide granule, wherein the substantially water soluble pesticide active agent has a water solubility of at least 10 g/L.

2. The process of claim 1 wherein the substantially water soluble pesticide active agent is dinotefuran.

3. The process of claim 1 wherein a first substantially soluble pesticide active agent and a second substantially soluble pesticide active agent are utilized.

4. An extruded pesticide granular composition, the composition comprising first extruded pesticide granules and second extruded pesticide granules and at least one non-ionic surfactant, wherein the first extruded pesticide granules include a substantially water soluble pesticide active agent different from a pesticide active agent in the second extruded pesticide granules, and wherein the substantially water soluble pesticide active agent in the first extruded granules has a water solubility of at least 10 g/L.

5. The extruded pesticide granular composition of claim 4 wherein the second extruded pesticide granules include a substantially water insoluble pesticide active agent, wherein the substantially water insoluble pesticide active agent has a water solubility of up to 10 g/L.

6. The extruded pesticide granular composition of claim 5 wherein at least one pesticide active agent is dinotefuran.

7. The extruded pesticide granular composition of claim 4 wherein the total amount of pesticide active agent is from 1 wt. % to 25 wt. %.

8. The extruded pesticide granular composition of claim 4 wherein the non-ionic surfactant comprises a block polymer comprising at least one polyethoxylate block and at least one poly-C3-C5-alkoxylate block.

9. The extruded composition of claim 4 wherein the non-ionic surfactant is a block polymer including a hydrophilic block and a hydrophobic block.

10. The extruded composition of claim 4 wherein the extruded composition includes urea in an amount of at least 50 wt %.

11. The extruded pesticide granular composition of claim 4 wherein the composition includes less than 1 wt. % water.

12. A method for controlling phytopathogenic fungi and/or undesired vegetation and/or undesired attack by insects or mites and/or for regulating the growth of plants, where the extruded pesticide granular composition of claim 4 is allowed to act on the respective pests, their environment or on the crop plants to be protected from the respective pests, on the soil and/or on undesired plants and/or on the crop plants and/or their environment.

* * * * *